United States Patent [19]
Chopra et al.

[11] Patent Number: 5,866,144
[45] Date of Patent: Feb. 2, 1999

[54] SKIN CLEANING COMPOSTITION

[75] Inventors: Suman K. Chopra, Dayton; Alan W. Kanowitz, Cartaret; Bret Schweid, Avenel, all of N.J.

[73] Assignee: Colgate-Palmolive Co., New York, N.Y.

[21] Appl. No.: 756,092

[22] Filed: Nov. 22, 1996

[51] Int. Cl.$^6$ ....................................................... A61K 7/48
[52] U.S. Cl. .......................... 424/401; 514/844; 514/975
[58] Field of Search ............................ 924/401; 514/844, 514/975

[56] References Cited

U.S. PATENT DOCUMENTS

| | | |
|---|---|---|
| 5,076,953 | 12/1991 | Jordan et al. . |
| 5,096,608 | 3/1992 | Small et al. . |
| 5,154,849 | 10/1992 | Visscher et al. . |
| 5,204,014 | 4/1993 | Redd et al. . |
| 5,225,097 | 7/1993 | Kacher et al. . |
| 5,225,098 | 7/1993 | Kacher et al. . |
| 5,227,086 | 7/1993 | Kacher et al. . |
| 5,262,079 | 11/1993 | Kacher et al. . |
| 5,264,144 | 11/1993 | Moruney et al. . |
| 5,264,145 | 11/1993 | French et al. . |
| 5,294,363 | 3/1994 | Schwartz et al. . |
| 5,300,249 | 4/1994 | Schwartz et al. . |
| 5,312,559 | 5/1994 | Kacher et al. . |
| 5,328,632 | 7/1994 | Redd et al. . |
| 5,340,492 | 8/1994 | Kacher et al. . |
| 5,395,541 | 3/1995 | Carpenter et al. . |
| 5,425,892 | 6/1995 | Taneri et al. . |
| 5,496,493 | 3/1996 | Cox et al. . |
| 5,510,050 | 4/1996 | Dunbar et al. . |

FOREIGN PATENT DOCUMENTS

| | | |
|---|---|---|
| 9113690 | 9/1909 | WIPO . |
| 9216610 | 10/1992 | WIPO . |

*Primary Examiner*—Jyothsna Venkat
*Attorney, Agent, or Firm*—Martin B. Barancik; James M. Serafino

[57] ABSTRACT

A solid composition which comprises
   a. about 27 to 38 wt. % of a mild synthetic anionic surfactant,
   b. about 18 to about 30 wt. % soap,
   c. about 27 to about 33 wt. % free fatty acid,
   d. about 1 to about 5 wt. % of paraffin wax, and
   e. the balance water.

1 Claim, No Drawings

SKIN CLEANING COMPOSTITION

BACKGROUND OF THE INVENTION

Basic skin cleaning activities have been long addressed by the personal care industry. Removing soil from the skin is a worldwide requirement of the consumer population that has been met by the available skin cleansing products. The consumer population is now looking for additional benefits beyond basic cleansing. Cleansing should be accompanied by a pleasant skin feel. It should be desirable to have a pleasant looking formulation which maintains its physical integrity substantially throughout use, particularly when in a solid form such as a bar. It should be as cost effective as possible.

It has now been discovered that a specific combination of a mild synthetic surfactant, preferably acylisethionate, soap, free fatty acid and a paraffin wax bring about a solid composition which has good lathering, conditioning, mildness, good hardness, slough and use-up values and is cost effective as well.

SUMMARY OF THE INVENTION

In accordance with the invention there is a solid composition which comprises
 a. about 27 to 38 wt. % of a mild synthetic anionic surfactant,
 b. about 18 to about 30 wt. % soap,
 c. about 27 to about 33 wt. % free fatty acid,
 d. about 1 to about 5 wt. % of paraffin wax, and
 e. the balance water.

It is preferred to use as the synthetic anionic surfactant an acylisethionate. However, up to about 25 wt. %, preferably up to about 20 wt. % of the acylisethionates can be replaced with other mild anionic surfactants.

The soap which is employed in the composition can be added totally as premade soap to the manufacturing process of the bar. However, it is preferred that at least some of the soap is made in situ during the bar manufacturing process. Therefore, when premade soap is added "neat" in the bar manufacturing process, it still has present about 30 wt. % water. This additional water brings about difficulty in processing. At least about 5 wt. % of the soap, as percent of the total composition, should be prepared in situ, preferably at least about 7 wt. %. For example, if 18 wt. % of soap is in final bar composition, then a minimum of 5/18 or 28% of the soap present is made in situ. All of the soap in the bar can be made in situ; however, this can add significantly to the overall cost. Generally, no more than about 25 wt. % of the soap, as percent of the total composition, is made in situ. Preferably, no more than about 22 wt. % of the soap is made in situ. The soap is made in situ during the bar manufacturing process by neutralization of fatty acids with a base such as sodium hydroxide or potassium hydroxide. This preferred method of placing soap into the final composition maintains the moisture level in an appropriate range while allowing the overall soap and free fatty acid to be in the beneficial range to bring about desired properties such as proper pH and mildness.

DETAILED DESCRIPTION OF THE INVENTION

The compositions of the invention are mild to the skin, have good hardness, slough, use-up and are cost effective as well as maintain at good levels various indicia of mildness, skin feel and lather. By mildness is meant less irritating to the skin than soap, as for example, measured by a skin barrier destruction test.

The mild anionic surfactant is important to the composition for it provides the lack of irritation and assists in the lather generation. Such surfactants have long chain alkyl groups having in general from about ten to about twenty carbon atoms, preferably about twelve to about eighteen carbon atoms. The alkyl groups are preferably normal. However, small quantities of branching can occur as well as unsaturation. This particularly occurs when the alkyl groups are derived from natural products. The positive counterion can be alkali metal cation such as sodium or potassium, ammonium or substituted ammonium such as triethanolammonium. Examples of the mild synthetic anionic surfactants include the alkylacylisethionates such as sodium cocoylisethionate, alkyltaurates, ethoxylated alkylglycerylsulfonates, alkylglyceryl ether sulfonates, alkylethoxylated sulfates, alkylsarcosinates, N-acylglutamates, alkyl sulfosuccinates, alkyl phosphate esters and the like and mixtures thereof. The preferred surfactant is alkylacylisethionate and that at least 75 wt. % of the synthetic anionic surfactant be an alkylacylisethionate.

The second component in the composition is soap. This is traditional soap, that is the salt of a long chain alkyl carboxylate. The cation and alkyl position can be as defined above for the synthetic anionic surfactant. Premanufactured soap can be mixed together with the rest of the materials and made into a bar by following the usual solid soap manufacturing procedures. However, it is preferable to have the amount of soap indicated above prepared by an in situ process in the bar manufacturing process. This is done by neutralization of fatty acid with a base such as sodium or potassium hydroxide, preferably sodium. This preferred method of placing soap into the final composition maintains the moisture level in an appropriate range while allowing the overall soap and free fatty acid to be in the beneficial range to bring about desired properties such as proper pH and mildness as well as providing relatively easy processing.

Free fatty acid is a long chain alkyl carboxylic acid having from about ten to about twenty carbon atoms, preferably about twelve to about eighteen carbon atoms.

The paraffin wax is an important part of this invention. It allows the quantity of higher priced bar components to be reduced as well as improving physical properties of the bar such as hardness, use-up and bar slough. Lather and mildness are essentially maintained when evaluated against previous similar syndet bars in the marketplace without paraffin wax. The paraffin wax presence also increases the phase stability during and after manufacturing and reduces the propensity to form a sandy, gritty bar. The paraffin wax has a melting point of from about 105° F. to about 200° F., preferably from about 125° F. to about 185° F., and most preferably from about 135° F. to about 165° F. A preferred paraffin wax is a fully refined petroleum wax which is odorless and tasteless and meets FDA requirements for use as coatings for food and food packages. Such paraffins are readily available commercially. A very suitable paraffin wax can be obtained, for example from The International Group, Inc., Wayne Pa.

The paraffin wax ingredient is optionally partially replaced by a microcrystalline wax. A suitable microcrystalline wax has a melting point ranging, for example, from about 140° F. (60° C.) to about 185° F. (85° C.), preferably from about 145° F. (62° C.) to about 175° F. (79° C.). The wax preferably should meet the FDA requirements for food grade microcrystalline waxes. A very suitable microcrystalline wax is obtained from Witco Chemical Company under the trade name Multiwax X-145A. These microcrystalline waxes are considered as part of the 1–5 wt. % paraffin wax since they are essentially purified waxes.

Other materials may be present in the bar such as preservatives, colorants, fragrances and the like in their usual small quantities. However, it is preferred to maintain the synthetic anionic surfactant and the soap as the primary surfactant system. Essentially very little, less than about 4 wt. % of the bar, preferably less than about 3 wt. % of the bar and most preferably zero wt. % of the bar should be any further surfactant.

The quantity of the components of the composition are significant to the properties. The mild synthetic anionic surfactant should be from about 27 to about 38 wt. % of the bar, preferably about 28 to about 37 wt. % and most preferably about 29 to about 36 wt. %. The soap portion of the composition is from about 18 to about 30 wt. %, preferably about 19 to about 29 wt. %, and most preferably about 20 to about 28 wt. %. The free fatty acid portion of the composition is from about 27 wt. % to about 33 wt. %, preferably about 28 to about 32 wt. %. The paraffin wax is from about 1 to about 5 wt. % of the composition. Compositions having about 4 wt. % or less perform well. It is preferred to have at least about 2 wt. % paraffin present. Compositions with 3 to 3.5 wt. % paraffin give good performance.

The pH of the composition as measured by pH meter of 1% product solution in water is from about 6.5 to about 8.5, preferably about 7.0 to about 8.1. The quantity of water is maintained at a minimum, generally from about 3 to about 8.5 wt. %, preferably about 4 to about 7 wt. % and most preferably about 5 to about 7 wt. %. The composition can be prepared by ordinary means as shown below following a preferred mode of preparation.

Stearic acid is melted in a Ross mixer and sodium cocoylisethionate along with preservative (EDTA Na4) is added. They are mixed at 200°–220° F. for 10 minutes. Sodium hydroxide is added to make in situ soap followed by addition of paraffin wax. Molten soap (moisture 30%) is added, and contents are mixed for an additional 10 minutes. Soap chips are then made by flaking on a chill roll mill. Soap chips are mixed together along with other ingredients (titanium dioxide, BHT & fragrance) in the amalgamator at 77°–86° F. and milled (twice), plodded and pressed into soap bars.

The compositions of the invention shown in the ensuing examples were made by the above procedure.

All Numbers Are In Wt. % Of The Composition

| Component | Control (marketed bar) | Example 1 | Example 2 |
|---|---|---|---|
| Sodium Cocoyl Isethionate | 49 | 30 | 35 |
| Soap (premanufactured) | 15 | 8 | 15 |
| Sodium Stearate (Manufactured in situ) | — | 19 | 6 |
| Stearic Acid | 25 | 30 | 30 |
| Hydrogenated Castor Oil | 1.0 | — | — |
| Paraffin Wax | — | 4 | 4 |
| BHT | 0.02 | 0.02 | 0.02 |
| Perfume | 1.5 | 1.5 | 1.5 |
| $TiO_2$ | 0.5 | 0.5 | 0.5 |
| EDTA-$Na^4$ | 0.01 | 0.01 | 0.01 |
| Water | QS | QS | QS |

The following tests are carried out utilizing the disclosed methodology.

Physical Testing

The formulations of the above table were tested for hardness, slough and use-up by the following methods.

Hardness: The bar hardness is determined using the needle penetrometer from Precision Scientific Co. The apparatus uses a 100 gram weighted needle point, and the depth of penetration into the soap surface is measured after a 10-second penetration interval. A minimum of nine data points are taken, and average results are given in millimeters. The results provide a relative assessment of bar hardness.

Slough Test: The weight of the bar is recorded in grams. The bars are washed twice for 30 seconds at 30 minute intervals at 100° F. before testing. The bar is placed in a soap dish (120 mm×75 mm×16 mm). The dish is filled with tap water and the bar remains in the water for 17 hours at 35°–40° C., at 100% relative humidity. At the end of 17 hours, the resulting soft material (slough) is removed using finger pressure. The bar is air-dried for 24 hours at 21°–25° C., after which the bar weight is recorded. The weight loss is determined as the weight loss per 100 grams.

Use-Up: In this method, the soap bars are repeatedly washed and then allowed to dry. The test is carried out over a 4-day period in order to simulate at-home usage. The initial weights of the bars prior to testing are recorded. A few different individuals washed the bars for 10-second intervals in warm tap water (90°–100° F.). The soap bars were placed in a soap dish with a grid to allow drainage of water between washings. The bars are allowed to dry for at least a 20-minute interval between washings. The soap bars undergo a total of 20 washes of 10-second duration over a 2 day period and are then dried for at least 24 hours prior to reweighing. The results were reported as weight loss per 100 grams.

Moisture (%): The moisture of the chip is measured by microwave heating. (Lab Wave 9000 by CEM Corporation)

pH (1% Solution of Bar in Water): The pH of a 1 wt. % product in water is measured by pH meter.

Mildness

In-Vitro

Collagen Swelling: 40 ml of a 1% solution of the evaluated bar actives are prepared from ultrapure water. This stock solution is spiked with tritium labeled water to give about 25,000 cpm/ml, i.e., approximately 1,000,000 cpm/40 ml.

Six pieces of collagen (Colla-Tec, Inc., N.J.) each weighing 10–25 mg (weighed to the fifth decimal place), are weighed into scintillation vials. Five milliliters of the tritium labeled product solution are added to each vial. The vials are incubated for 48 hours at 50° C. After incubation, the collagen pieces are removed and rapidly rinsed in a large volume of water (about 1 liter) to remove excess detergent and/or label on the film surface. Each swollen piece of collagen is digested with 1 ml of 2M NaOH for about 1 hour at 80° C., until the solution is clear. The vials are then cooled to room temperature, 10 ml of scintillation cocktail (Ecolume (ICN biochemicals)) and 250 microliter of concentrated perchloric acid are added, and the vials are vortexed to give a clear solution. The tritium concentration in the vials are then counted. The collagen swelling values (ml of water uptake/g collagen) are calculated using the dpm values (disintegration per minute) and the known activity of the stock solution (determined by measuring the dpm/ml of the stock solution, in triplicate). Comparison of collagen swelling values, and therefore predicted irritation potential, between samples are done using an analysis of variance (ANOVA).

Sensory

A group of ten judges trained in the sensory evaluations take part in the test. The evaluations are conducted using a paired comparison forced choice design. Replicate evaluations are conducted for each pair of products. Using a standard hand wash procedure, the judges evaluate the slip and smooth surface of the wet bar, the amount of lather, fastness to lather, creamy lather and thick lather. After the fourth wash using a standard arm wash procedure, the judges also evaluate their skin on fastness of rinse, drag, stickiness, oiliness and residue on wet skin and the tight, dry, smooth, softness, stickiness, drag, oiliness and treated feeling on dry skin at immediate, ten and thirty minutes after drying. All evaluations are performed under 98°±2° F. and water hardness of approximately 265 ppm. A binomial test of significance is conducted on the data.

Below are the results:

| Test System | Control | Example 1 | Example 2 |
|---|---|---|---|
| Physical Testing | | | |
| Hardness (mm) | 3.93 ± 0.22 | 3.76 ± 0.3 | 3.21 ± 0.19 |
| Slough (%) | 25.0 ± 2.73 | 12.4 ± 2.57 | 16.9 ± 0.41 |
| Use Up (%) | 27.8 ± 1.12 | 18.9 ± 0.41 | 27.1 ± 0.26 |
| Moisture | 6.5 | 7.7 | 7.1 |
| pH (1% solution) | 7.6 | 7.7 | 8.0 |
| Mildness | | | |
| In Vitro | | | |
| Collagen Swelling | — | Parity to control | Parity to control |
| Sensory | | | |
| Overall Lather | Parity to Dove | Parity to control | Parity to control |
| Overall Skin Feel | Parity to Dove | Parity to control | Parity to control except for less conditioning but cleaner rinsing |

What is claimed is:

1. A solid composition which comprises a. about 27 to 38 wt. % of sodium cocoylisethionate;

b. about 18 to 30 wt. % soap;

c. about 27 to about 33 wt. % free fatty acid;

d. about 1 to about 5 wt. % of paraffin wax; and e. the balance water, with the proviso that no surfactant is present in the composition other than soap and sodium cocylisethionate.

\* \* \* \* \*